(12) United States Patent
Golubovic et al.

(10) Patent No.: US 7,777,012 B2
(45) Date of Patent: Aug. 17, 2010

(54) METHOD OF PREPARING A PROTEIN AGGREGATE AND A PHARMACEUTICAL PREPARATION

(75) Inventors: Marijana Golubovic, Delft (NL); Marcel Ottens, Leiden (NL); Geert Jan Witkamp, Bergschenhoek (NL); Lucas Antonius Maria Van Der Wielen, Bleiswijk (NL)

(73) Assignee: Technische Universiteit Delft (NL)

( * ) Notice: Subject to any disclaimer, the term of this patent is extended or adjusted under 35 U.S.C. 154(b) by 536 days.

(21) Appl. No.: 10/598,953

(22) PCT Filed: Mar. 15, 2005

(86) PCT No.: PCT/NL2005/000192

§ 371 (c)(1),
(2), (4) Date: Dec. 27, 2007

(87) PCT Pub. No.: WO2005/087016

PCT Pub. Date: Sep. 22, 2005

(65) Prior Publication Data

US 2008/0274953 A1     Nov. 6, 2008

(30) Foreign Application Priority Data

Mar. 15, 2004  (NL) .................................. 1025723

(51) Int. Cl.
*A23J 1/00* (2006.01)

(52) U.S. Cl. ....................................................... 530/418
(58) Field of Classification Search ....................... None
See application file for complete search history.

(56) References Cited

U.S. PATENT DOCUMENTS

| 5,288,856 A | 2/1994 | Amiguet |
| 5,981,719 A | 11/1999 | Woiszwillo et al. |
| 6,413,749 B1 | 7/2002 | Becker et al. |

FOREIGN PATENT DOCUMENTS

| WO | WO 98/06279 | 2/1998 |
| WO | WO 01/00041 | 1/2001 |
| WO | WO 03/076456 A2 | 9/2003 |

OTHER PUBLICATIONS

Hofland et al., "Isoelectric Precipitation of Soybean Protein Using Carbon Dioxide as a Volatile Acid", Journal of Chromatography B, 743: 357-368 (2000).

*Primary Examiner*—Suzanne M. Noakes
(74) *Attorney, Agent, or Firm*—Akerman Senterfitt

(57) ABSTRACT

The invention relates to a method of preparing a protein aggregate, wherein an aqueous protein solution is acidified with a pH that lies above the isoelectric point of the protein. In accordance with the invention, a first protein, which through acidification is able to form a protein aggregate, is acidified in the presence of a second protein in the aqueous solution in order to form a coaggregate comprising the first and second protein, wherein the second protein under identical temperature conditions and pH does not form a protein aggregate in the absence of the first protein. Acidification preferably occurs with the aid of $CO_2$.

7 Claims, No Drawings

METHOD OF PREPARING A PROTEIN AGGREGATE AND A PHARMACEUTICAL PREPARATION

The invention relates to a method of preparing a protein aggregate, which method comprises the acidification of an aqueous solution of the protein, wherein the pH of the solution lies above the isoelectric point of the protein.

Such a method is known from WO 01/000041 (PCT/NL00/00451). This patent specification describes how a protein aggregate can be formed, for example, on the basis of a soybean protein. The technique described, wherein acidification occurs through the addition of $CO_2$ under an above-atmospheric pressure, affords excellent control over the formation of protein aggregate. For example, it describes the possibility of fractionated precipitation of some of the soybean proteins. Potential applications mentioned include foodstuffs and excipients.

The object of the present invention is to provide a method with an increased applicability.

To this end the method according to the invention is characterised in that a first protein, which through acidification is able to form a protein aggregate, is acidified in the presence of a second protein in the aqueous solution in order to form a coaggregate comprising the first and second protein wherein, under identical temperature conditions and pH, the second protein does not form a protein aggregate in the absence of the first protein.

Acidification to approximately the isoelectric point does not enable every protein to form a protein aggregate. Surprisingly, some proteins were shown to coaggregate in the presence of a first protein that is able to form aggregates under the conditions wherein that first protein forms a protein aggregate. In the context of the present invention, such proteins are second proteins. Of course, whether a protein has the ability to function as the second protein must be established by experiment, but since there is a variety of first proteins, it suffices to carry out a simple series of tests in order to find a first protein that is suitable for the coaggregation of the second protein. Without being tied to any theory, it is believed that the ability to become coaggregated depends on specific interactions between the first and the second protein, which are subject to, for example, hydrophobic interactions, complementary charges and also the isoelectric point of the second protein. The resulting precipitates are, for example, industrially applicable. The acid used is preferably a volatile acid, so that it can be removed again. Otherwise or in addition, the acid is preferably a pharmaceutically acceptable acid such as acetic acid.

According to an important embodiment, the method according to the invention is characterised in that the first protein is obtained from a first source, and the second protein from a second source.

This will be of particular interest with regard to pharmaceutical applications such as pharmaceutical applications for human use, wherein the second protein is, for example, a human protein and the first protein a non-human protein. In the context of the invention the term source is understood to mean that the protein may be manufactured synthetically (by means of organic synthesis in a cell-free system that makes use of a ribosome system that may or may not be artificial) or it may be manufactured naturally by cells that may or may not be genetically manipulated, or by a single celled or multicelled organism, which protein is subsequently isolated.

An important embodiment is characterised in that acidification occurs by placing the aqueous protein solution into a $CO_2$ atmosphere, wherein under identical conditions of temperature, concentration and pressure, the second protein does not form a protein aggregate.

In contrast with other known techniques regarding coaggregation or coprecipitation, such as precipitation with ammonium sulphate or acetone, the aggregate formed with the aid of the invention will be free from non-gaseous aggregation additives. There is also a reduced risk of denaturation. The round shape of the obtained protein precipitate may be further favourable with regard to the manageability of the precipitated protein particles, the mouth feeling (organoleptic properties), and for the release of the second protein in medicinal applications. Although a second protein is mentioned in the present application, the use of a third, etc. protein complying with the conditions for coaggregation as described for the second protein, is also included in the invention.

According to a preferred embodiment, the $CO_2$ pressure is increased to the highest value within ten seconds.

In accordance with the invention, the formed coprecipitates may optionally be stabilised with the aid of a crosslinker.

Acidification for the purpose of forming the protein coaggregate preferably takes place while stirring.

This facilitates the admixture of the acid, for example in the form of $CO_2$, to the solution. Depending on the characteristics of the second protein, care must obviously be taken to avoid denaturation caused by stirring too vigourously. Any suitable manner of stirring may be used (shaking, magnetic stirring, swivelling, etc.).

According to an important embodiment, the second protein used is a pharmacologically active protein.

The invention also relates to a pharmaceutical composition comprising a coaggregate of a first protein which can form an aggregate through acidification, and a second protein, which does not form an aggregate under the conditions where the first protein forms an aggregate through acidification, wherein the second protein is a pharmacologically active protein.

The coaggregate is preferably formed with the aid of a volatile acid and most preferably with $CO_2$.

The present invention will now be further elucidated by way of the following exemplary embodiment.

EXAMPLES

Material

*Candida rugosa* lipase (lyophilised powder; type VII, product no. L1754) was obtained from Sigma-Aldrich, Zwijndrecht, Netherlands. Isoelectric point=5.2.

Lipase from pig's pancreas (type II, product no. 3126) was obtained from Sigma-Aldrich. Isoelectric points of the isoenzymes: 4.9 and 5.0.

The soybean protein powder was degreased soybean powder (S-9633, Sigma-Aldrich). Isoelectric points of the main components: glycinin ~4.9-5.2; β-conglycinin: ~4.7-5.0. Prior to use, the soybean protein powder is dissolved in Milli-Q water (10% w/w) and the pH of the solution is adjusted to 9 by adding 1.0 M NaOH. After stirring for 40 minutes, the suspension is centrifuged (2 h, 4000 g) and the supernatant is used for the experiments. The protein concentration is 40 g/l.

Lipase Assay

Assay buffer: 100 mM sodium phosphate buffer, pH 7.4.

Reagent: p-nitrophenylpropionate; 7.8 mg in 1 ml ethanol. 10 µl per ml assay buffer.

Assay conditions. 25° C.

Spectrophotometric absorption: 405 nm.

Example 1

Control

A) Precipitation of Lipase and Soybean Protein Using $CO_2$.

2 ml of a solution of 100 mg/ml lipase in 10 mM sodium phosphate buffer (pH=8) were introduced into a test-tube. 2 ml in Milli-Q-diluted soybean protein solution (end concentration 20 g/l) were introduced into a test-tube. The tubes were kept for 40 minutes in a pressure vessel at a pressure of 10 bars $CO_2$. Upon return of the pressure vessel to ambient pressure, the tubes were visually inspected for the presence of a precipitate. Only the tubes containing soybean protein exhibited a precipitate.

B) Precipitation of Lipase and Soybean Protein with the Aid of Sulphuric Acid.

1 g of lipase was dissolved in 10 ml Milli-Q water, after which the pH was adjusted to 8 with 1 M NaOH.

40 g of soybean protein were dissolved in 1 l water and the pH subsequently adjusted to 8 with 1 M NaOH.

Using a magnetic stirrer, 0.1 M $H_2SO_4$ was admixed to each of the solutions until the pH was 4. Only soybean protein produced a visually detectable precipitate.

Example 2

In Accordance with the Invention 0.5 g of lyophilised lipase from *Candida rugosa* were dissolved in 50 ml of a solution (pH=10.2) of 20 g of soybean protein per litre of water. Thus the weight ratio lipase to soybean protein was 1:2. Precipitation was conducted in a 50 ml (volume available for experiments) pressure-resistant glass vessel equipped with a magnetically coupled stirrer. The inside diameter of the vessel was 51 mm. The stirrer turbine had six blades, diameter 34 mm, mounted at 5 mm from the bottom of the vessel. Stirring rate: 300 rpm. The carbon dioxide was adjusted with the aid of a pressure regulator. The pH, the pressure and the temperature were determined on-line.

The $CO_2$ pressure was adjusted within 10 seconds to 11.2 bars. The temperature was 20.2° C. and after applying the pressure it was 20.4° C.

Application of the $CO_2$ pressure causes the pH to drop to 5. After 45 minutes the vessel was depressurised and an assay was performed on the suspension obtained by the treatment and on the supernatant obtained after centrifugation, in order to determine the percentage of coprecipitated lipase. 10% of the lipase activity appeared to have precipitated, which was confirmed by measuring the activity in the pellet.

In a comparable experiment using lipase from the pig's pancreas, 30% of the lipase activity was found in the pellet.

The invention claimed is:

1. A method of preparing a protein coaggregate, comprising the acidification of an aqueous protein solution having a first and a second protein,
    wherein the pH of the solution lies above the isoelectric point of both of the proteins,
    wherein said first protein, which through acidification is able to form a protein aggregate, is acidified in the presence of a second protein in the aqueous solution in order to form a coaggregate comprising the first and second protein,
    and wherein, under identical temperature conditions and pH, the second protein does not form a protein aggregate in the absence of the first protein.

2. The method according to claim 1, wherein the first protein is obtained from a first source and the second protein is obtained from a second source.

3. The method according to claim 1, wherein acidification occurs by placing the aqueous protein solution under a $CO_2$ atmosphere, wherein under identical conditions of temperature, concentration and pressure, the second protein does not form a protein aggregate in the absence of the first protein.

4. The method according to claim 3, wherein the $CO_2$ pressure is raised within 10 seconds to the highest value.

5. The method according to claim 1 further comprising stabilizing the coaggregates through the addition of a cross-linker.

6. The method according to claim 1, wherein the second protein used is a pharmacologically active protein.

7. The method according to claim 3, wherein the formation of the protein coaggregate by acidification with $CO_2$ further comprising stirring the solution.

* * * * *